(12) United States Patent
Matityaho (10) Patent No.: US 12,002,577 B2
(45) Date of Patent: Jun. 4, 2024

(54) APPARATUS, SYSTEM AND METHODS FOR MANAGEMENT OF MEDICAL SUPPLIES

(71) Applicant: IDENTI HEALTHCARE LTD., Netanya (IL)

(72) Inventor: Shlomo Matityaho, Tel-Mond (IL)

(73) Assignee: IDENTI HEALTHCARE LTD., Netanya (IL)

( * ) Notice: Subject to any disclaimer, the term of this patent is extended or adjusted under 35 U.S.C. 154(b) by 332 days.

(21) Appl. No.: 17/429,907

(22) PCT Filed: Feb. 20, 2020

(86) PCT No.: PCT/IL2020/050186
§ 371 (c)(1),
(2) Date: Aug. 10, 2021

(87) PCT Pub. No.: WO2020/170250
PCT Pub. Date: Aug. 27, 2020

(65) Prior Publication Data
US 2022/0130528 A1 Apr. 28, 2022

Related U.S. Application Data (60) Provisional application No. 62/809,102, filed on Feb. 22, 2019.

(51) Int. Cl.
*G06K 9/00* (2022.01)
*G06V 10/20* (2022.01)
(Continued)

(52) U.S. Cl.
CPC ........... *G16H 40/40* (2018.01); *G06V 10/255* (2022.01); *G06V 20/52* (2022.01); *G16H 40/20* (2018.01)

(58) Field of Classification Search
CPC ...... G06V 10/19; G06V 10/225; G06V 10/44; G06V 10/467; G06V 30/10;
(Continued)

(56) References Cited

U.S. PATENT DOCUMENTS 8,242,914 B2    8/2012  Matityaho et al.
9,129,054 B2 *  9/2015  Nawana .................. G16H 50/50
(Continued)

FOREIGN PATENT DOCUMENTS

WO    WO-2016109726 A1 *  7/2016  ............. A61B 17/16
WO       2019010462 A1     1/2019

OTHER PUBLICATIONS

PCT Search Report for International Application No. PCT/IL2020/050186 dated Jun. 14, 2020, 5 pp.
(Continued)

*Primary Examiner* — Shervin K Nakhjavan
(74) *Attorney, Agent, or Firm* — The Roy Gross Law Firm, LLC; Roy Gross (57) ABSTRACT

Systems and methods are provided for operating room inventory management by which an imaging stand has a base receptacle on which to place surgical utensils, a post rising above the base receptacle, a camera mounted at the top of the post, and one or more processors configured to acquire a procedure identifier input and an image from the camera, to identify in the image one or more recognition features of a surgical item, and to either: determine from the recognition features an inventory identifier of the surgical item to record use of the surgical item, or to determine that the recognition features are insufficient to determine an inventory identifier and to transmit the image for manual identification of the surgical item.

16 Claims, 4 Drawing Sheets

(51) Int. Cl.
*G06V 20/52* (2022.01)
*G16H 40/20* (2018.01)
*G16H 40/40* (2018.01)

(58) Field of Classification Search
CPC ......... G06V 30/1448; G06V 2201/034; G06V 10/255; G06V 20/52; G16H 10/65; G16H 40/20; G16H 40/40; G16H 30/40
See application file for complete search history.

(56) References Cited

U.S. PATENT DOCUMENTS

| | | | |
|---|---|---|---|
| 10,117,722 | B2 | 11/2018 | Sweeney |
| 10,198,818 | B2 * | 2/2019 | Varadarajan ............... G06T 7/11 |
| 10,517,680 | B2 * | 12/2019 | Moctezuma ........... A61B 90/90 |
| 10,528,840 | B2 * | 1/2020 | Bailey .................. G06V 20/647 |
| 10,910,103 | B2 * | 2/2021 | Venkataraman ....... A61B 34/37 |
| 11,583,360 | B2 * | 2/2023 | Amanatullah ......... A61B 90/06 |
| 2004/0186683 | A1 * | 9/2004 | Farber ................. G06Q 10/087 606/1 |
| 2010/0039513 | A1 | 2/2010 | Glickman et al. |
| 2012/0274842 | A1 | 11/2012 | Cordes |
| 2012/0316987 | A1 | 12/2012 | DeBusk et al. |
| 2013/0113929 | A1 * | 5/2013 | DeLand .................. A61B 90/90 382/103 |
| 2014/0081659 | A1 * | 3/2014 | Nawana ............... A61B 5/4833 705/3 |
| 2015/0149330 | A1 * | 5/2015 | Sweeney .............. G06Q 10/087 705/28 |
| 2015/0305735 | A1 * | 10/2015 | Gorek .................... A61B 90/53 606/147 |
| 2018/0064508 | A1 | 3/2018 | Sweeney |
| 2018/0247024 | A1 * | 8/2018 | Divine ................... G16H 40/20 |
| 2019/0201126 | A1 * | 7/2019 | Shelton, IV ........... G16H 20/40 |
| 2020/0143195 | A1 * | 5/2020 | Montano ................ G06Q 10/08 |

OTHER PUBLICATIONS

PCT Written Opinion for International Application No. PCT/IL2020/050186 dated Jun. 14, 2020, 4 pp.

* cited by examiner

APPARATUS, SYSTEM AND METHODS FOR MANAGEMENT OF MEDICAL SUPPLIES

CROSS REFERENCE TO RELATED APPLICATIONS

This application is a National Phase of PCT Patent Application No. PCT/IL2020/050186 having International filing date of Feb. 20, 2020, which claims the benefit of priority of U.S. Provisional Patent Application No. 62/809,102, filed Feb. 22, 2019, the contents of which are all incorporated herein by reference in their entirety.

FIELD OF THE INVENTION

The invention relates generally to inventory management, and in particular to management of inventory in the field of health care.

BACKGROUND

Operating room (OR) activities must be performed efficiently and with great care to ensure the health of patients undergoing surgery. Accurate recording of items used in OR for surgery is a vital aspect of maintaining hospital preparedness. Consequently, automating the task of recording item usage can enable OR personnel to devote their attention to other critical tasks. A variety of techniques exist for inventory recording, such as radio-frequency identification (RFID) tags and bar codes. However, not all supplies are tagged by these methods. Also, personnel must spend time applying different recording methods for different types of supplies. Improved automation would improve OR operations, resulting in higher standards of care and in economic savings.

SUMMARY

Embodiments of the present invention provide apparatus, systems, and methods of operating room inventory management. In some embodiments, a system is provided including: an imaging stand, having a base receptacle on which to place surgical utensils, a post rising above the base receptacle, and a camera mounted at the top of the post, such that surgical items placed on the base receptacle are in the depth of field of the camera. The system may also include an interactive user device including an interactive display; and one or more processors and memory storage, the memory storage including instructions that when executed by the one or more processor implement automated steps, as follows: acquiring a procedure identifier input; acquiring an image from the camera; and identifying in the image one or more recognition features of a surgical item. Subsequent steps may include either: determining, from the recognition features, an inventory identifier of the surgical item and transmitting a message to a hospital inventory system to record use of the surgical item; or determining that the recognition features are insufficient to determine an inventory identifier and transmitting the image to an application for manual identification of the surgical item.

In some embodiments, the one or more recognition features may include one or more of printed text, a printed graphical image, and a barcode. Alternatively or additionally, the one or more recognition features may include at least one of a length, width, color and shape of the surgical item. Acquiring the image may include acquiring a new image after detecting a sequence of changing images, wherein the new image is one of a sequence of static images. Acquiring the image may also include receiving the image from a video stream transmitted from the camera, and responsively determining by an image processing algorithm the presence of the surgical item in the image. In some embodiments, the one or more processors and memory storage are integrated into the imaging stand or into a mobile device.

In some embodiments, the imaging stand further includes a transmitter for transmitting data from the camera to the interactive device, which may be a mobile device.

Acquiring the procedure identifier input may include acquiring a procedure type identifier and acquiring one or more staff identifiers. Acquiring the procedure identifier input may include acquiring input entered by a user to the interactive user device.

The interactive user device may be configured with a mobile application that displays the image and the inventory identifier to confirm determination of the inventory identifier. The mobile application may be further configured to display the image without an inventory identifier to indicate that an image identifier was not determined.

In further embodiments, the one or more processors are processors of the interactive user device. Alternatively or additionally, the one or more processors are cloud-based processors and/or are integrated into the imaging stand.

Determining an inventory identifier of the surgical item may also include providing a user notification of image capture, wherein the user notification comprises one or more of a sound and a visual indicator.

Determining the inventory identifier may include completing a partial inventory identifier according to a predefined completion template.

In some embodiments, the message is a first message and the steps further include sending a second message to a supplier procurement system to order the surgical item. The recognition features may also include an RFID code acquired by an RFID reader of the imaging stand.

There may also be provided, by further embodiments of the present invention, a method for managing surgical inventory in an operating room (OR), implemented by one or more processors and memory storage, the memory storage including instructions that when executed by the one or more processor implement the steps of: acquiring a first image of a surgical item placed on a receptacle of an imaging stand prior to their entering the OR; acquiring a procedure identifier input; acquiring an image from a camera of the imaging stand; identifying in the image one or more recognition features of the surgical item; determining, from the recognition features, an inventory identifier of the surgical item; and transmitting a message to a hospital inventory system to record the use of the surgical item.

BRIEF DESCRIPTION OF DRAWINGS

For a better understanding of various embodiments of the invention and to show how the same may be carried into effect, reference will now be made, by way of example, to the accompanying drawings. Structural details of the invention are shown to provide a fundamental understanding of the invention, the description, taken with the drawings, making apparent to those skilled in the art how the several forms of the invention may be embodied in practice. In the accompanying drawings.

DETAILED DESCRIPTION

It is to be understood that the invention and its application are not limited to the methods and systems described below or to the arrangement of the components set forth or illustrated in the drawings, but are applicable to other embodiments that may be practiced or carried out in various ways.

Embodiments of the present invention provide methods and systems for monitoring operating room (OR) inventory.

Figure 1:
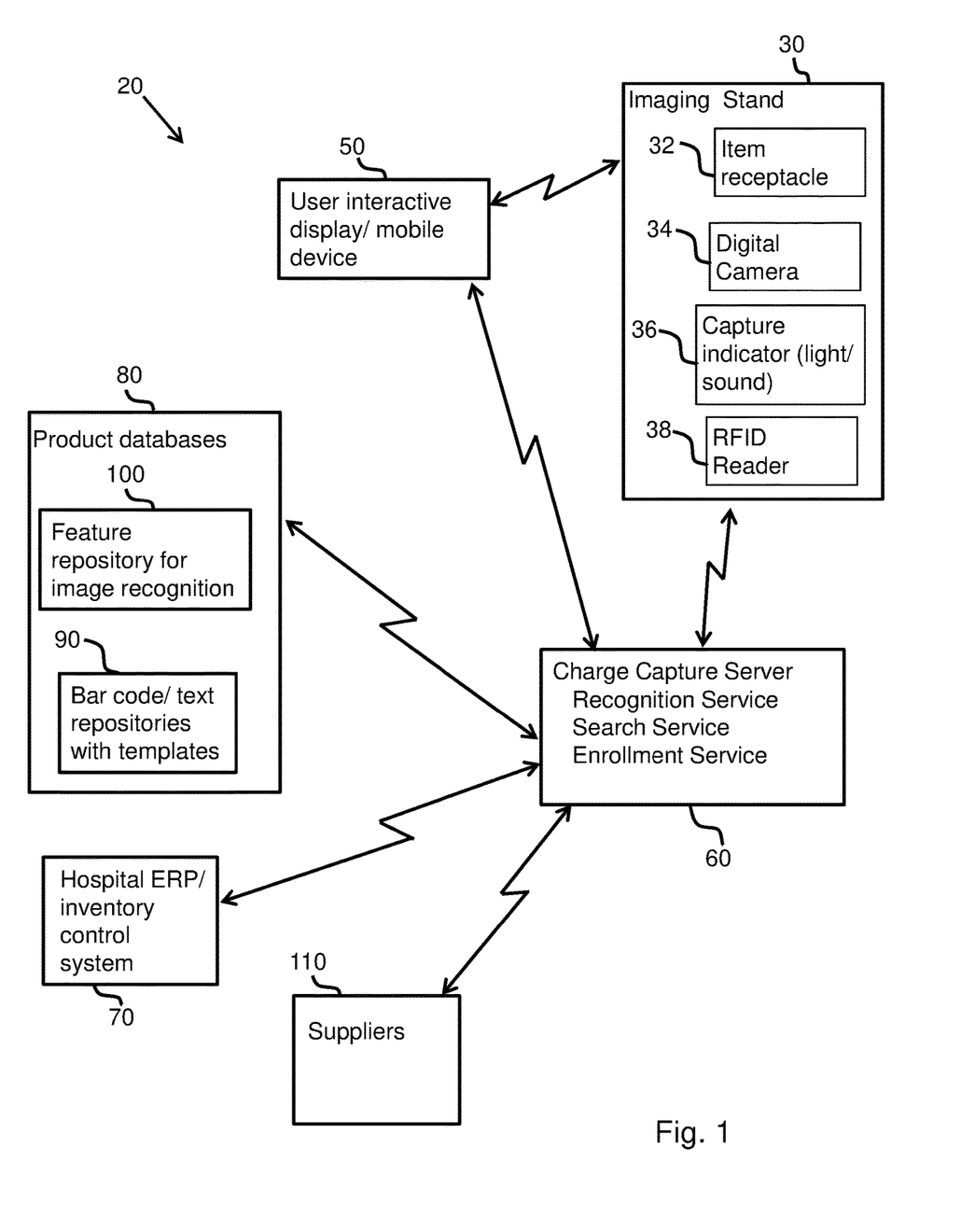
FIG. 1 is a schematic block diagram of a system for monitoring operating room (OR) inventory, according to some embodiments of the present invention.

FIG. 1 is a schematic block diagram of a system 20 for managing operating room inventory, according to some embodiments of the present invention.

The system 20 is designed to efficiently record usage of items applied during surgery, also referred to as the process of "charge capture", in particular of surgical implants, which are typically high value medical components and which are therefore typically tracked by hospital inventory systems. Such surgical components are often reordered from medical suppliers after each use, as opposed to disposable items, such as such as gloves and wipes, which are used in most procedures and are not typically tracked.

In embodiments of the present invention, system 20 includes an imaging stand 30, which is usually located in an operating room, or at the entrance to the operating room. The imaging stand includes a receptacle 32 onto which surgical items may be placed before the surgical procedure begins, in order to record (i.e., "charge") the items. The imaging stand may also be employed to "enroll" items, i.e., to register items in a product database.

Imaging stand 30 typically includes a digital camera 34, configured to capture images of items placed on the receptacle and to transmit the images to other processing elements of the system. The imaging stand may also include a capture indicator 36, which may be a light and/or a speaker, which indicates to a user that an image of an item placed on the receptacle has been successfully captured. In some embodiments, the capture indicator is a bi-color LED, configured to emit a red light while an item is being placed on the imaging stand (i.e., while there is motion on the receptacle) and then to emit a green light when a static image of the item has been captured. A speaker may be included, alternatively or in addition to the light, to indicate by a sound that an image an item has been successfully captured. The imaging stand may also include an RFID reader, which captures RFID information to complement the captured image. Hereinbelow, descriptions of image data transmission are assumed to include captured RFID data, if such data is available.

In some embodiments, system 20 also includes a user interactive device 50, which typically includes a processor, memory, and an interactive display. The interactive device may be affixed or integrated into the imaging stand or may be a separate mobile device. The interactive device may be programmed to receive information about a surgical procedure from a user (i.e., someone participating in the surgical procedure, such as an OR nurse). Information may include a surgical procedure type or number, and/or identifying information about staff who are participating in the surgical procedure, such as one or more surgeons performing the surgery. The surgical information may then be associated with the items recorded by the imaging stand in subsequent messages transmitted from the interactive device. An indication of image capture may also be provided by the mobile device, by a sound, a notification light, and/or the appearance of the captured image on the display of the mobile device itself. (That is, the capture indicator 36 may be provided by the mobile device.)

System 20 also typically includes a "charge capture server" 60, which receives the images of the items recorded by the camera 34 and identifies those items in a hospital inventory system 70. In some embodiments, the interactive device 50 is configured to send images to the charge capture server 60. Alternatively, the imaging stand 30 may be configured to directly send images to the charge capture server 60.

The charge capture server 60 may be located within a hospital or may be located remotely, and may also include distributed processing components, such that some steps of processing are performed locally and others remotely. In some embodiments, the charge capture server is implemented as a cloud-based service, which may support operations of multiple operating rooms in multiple hospitals. As described further herein, the charge capture server 60 typically includes two services, a recognition service for identifying recognizable features of items in an image, and a search service, which, based on the recognized features, searches product databases to identify and to record the item. The recognition service may be configured to recognize and decode recognition features of an item itself or of an item's packaging, if an item is placed on the imaging stand while still in its packaging. Recognition features may include standard linear barcodes, data matrices (such as 2D barcodes), and other symbols, as well as graphical images, such as logos. The recognition service may also perform optical character recognition (OCR) using methods known in the art, including algorithms for hard-to-read characters. Geometric features of items, such as size, color, and shape may be identified by image processing functions, which may include processes such as: rotation and warping, edge enhancement, binary and grayscale morphology, template and pattern recognition, object orientation detection by line intersection, point-to-point distance, point-to-line normal, and blob analysis. Geometric pattern matching may also include pattern filtering to extract item features in noisy images. Color-based dimensional gauging may also be performed. In some embodiments, the recognition service may also recognize multiple individual items on the receptacle.

Recognition may rely on templates, feature definitions, and product codes stored in one or more product databases 80. The product databases may include product codes 90 correlated with catalog identifying information (e.g., catalog codes and manufacturer IDs) and a geometric feature repository 100, which correlates product shapes, colors, sizes, etc. to catalog identifying information. The product databases may include interfaces to Medicaid Management Information Systems, such as McKesson EIS and Infor CloudSuite Healthcare, including receipt of catalog data, prices, item descriptions and updates.

After a recognition feature of an item is identified by the charge capture server, the charge capture server may provide the identifying information to a search service, which performs search queries of the product databases 80 to confirm the identity of the item. Typically the product databases include both hospital owned and vendor consigned implant inventory catalogues.

Once the item is identified by the search as a registered product in the database, the charge capture server 60 may then transmit a message, indicating that the item has been used in a surgical procedure, to a hospital ERP system 70. The ERP system may record the use of the item for purposes such as patient billing and clinical trial tracking. In addition, the charge capture server 60 may notify supplier procurement systems 110 of the item's use, in order that replacement items may be automatically requisitioned. Messages may conform to the Global Trade Item Number (GTIN, e.g. standards such as EAN13 or UPC12) and the Electronic Product Code (EPC) standard numbering schemes for identifying items.

If, conversely, the item is not found by the search service, the search service may repeat the search, based on alternative recognized features acquired in the image, as described further hereinbelow. As described above, the recognized features may also include a code recognized by an RFID reader.

In the event that all possible recognition attempts have been applied unsuccessfully, meaning the item cannot be identified by automated methods, the charge capture server directs the image data and the information acquired by the recognition service to an application for manual review of the image by back-office staff. The application is also referred to herein as an "enrollment service," which presents the image and the information to back-office staff, who manually determine the identity of the item. This may include reviewing the supply chain for the provision of items for the given surgical procedure. The identification may have failed because the item is not registered in the database, in which case the enrollment service application provides a form for the back-office staff enter ("enroll") the item into the database. By transferring the work to back-office staff, the task of determining a registered identity of an item is no longer placed on surgical staff (i.e., nurses), thereby facilitating greater efficiency in the operating room. Examples of the back-office interface are provided hereinbelow with respect to FIGS. 4A-4B.

Figure 2:
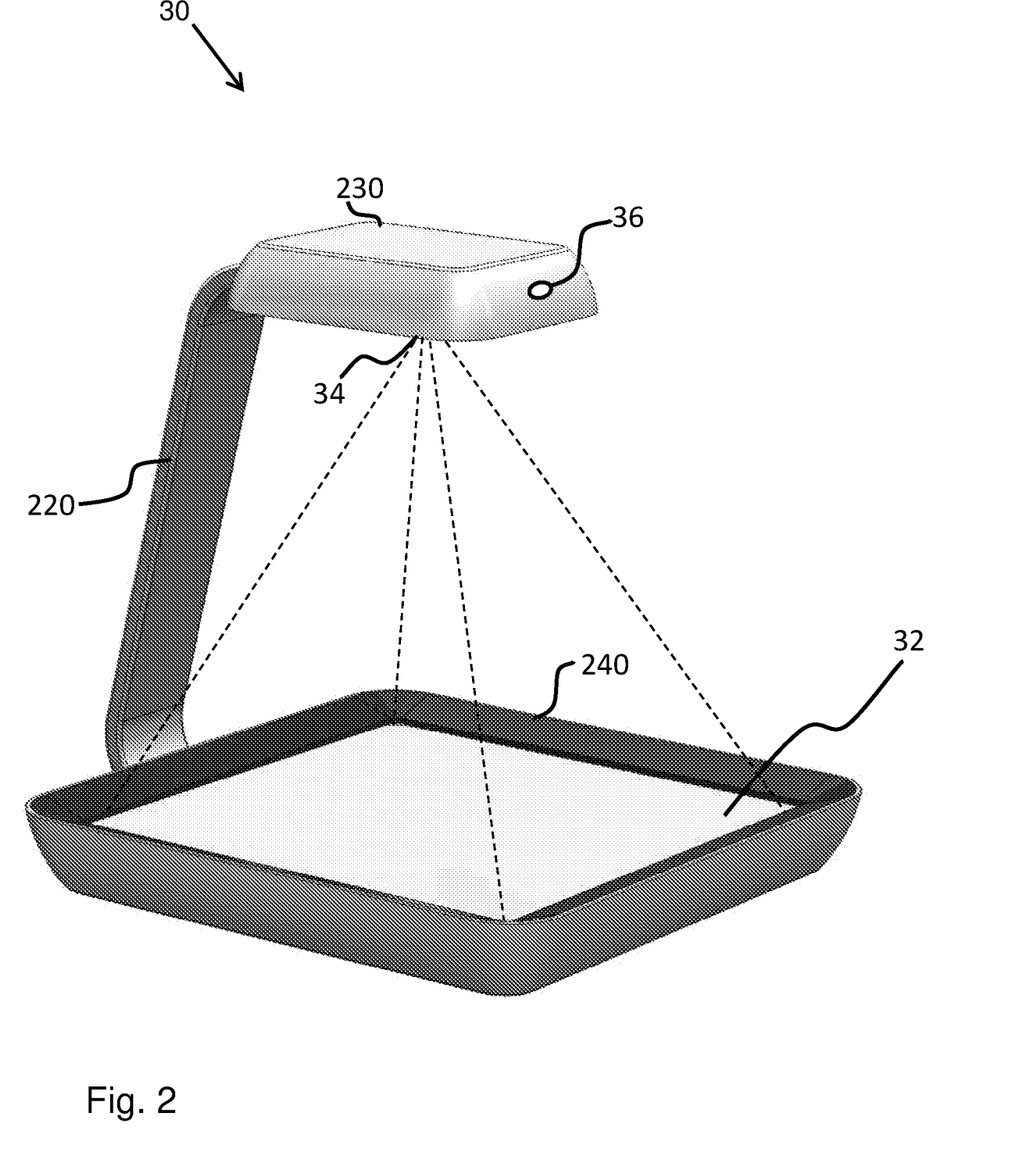
FIG. 2 is a schematic diagram of apparatus for managing OR inventory, according to some embodiments of the present invention.

FIG. 2 is a schematic illustration of an imaging stand 30 for managing operating room inventory, according to some embodiments of the present invention. As indicated in the figure, the imaging stand includes elements described above with respect to FIG. 1: the receptacle 32 onto which surgical items may be placed before the surgical procedure begins; the digital camera 34, configured to capture images of items placed on the receptacle and to transmit the images to other processing elements of the system; and the capture indicator 36, which may be an LED and/or microphone. In addition, the imaging stand typically includes an upright support or post 220, connecting between the receptacle at the base of the imaging stand to a stand top 230, which includes the digital camera 34. Lenses of the digital camera are typically configured such that the entire receptacle is within the image frame and depth of field of the camera.

Typically a ridge 240 surrounds the receptacle to prevent items from being place in a manner extending beyond the camera's image frame. Although the shape of the receptacle is indicated in the figure as being square, other polygonal shapes may be used, as well as a circular shape.

Figure 3:
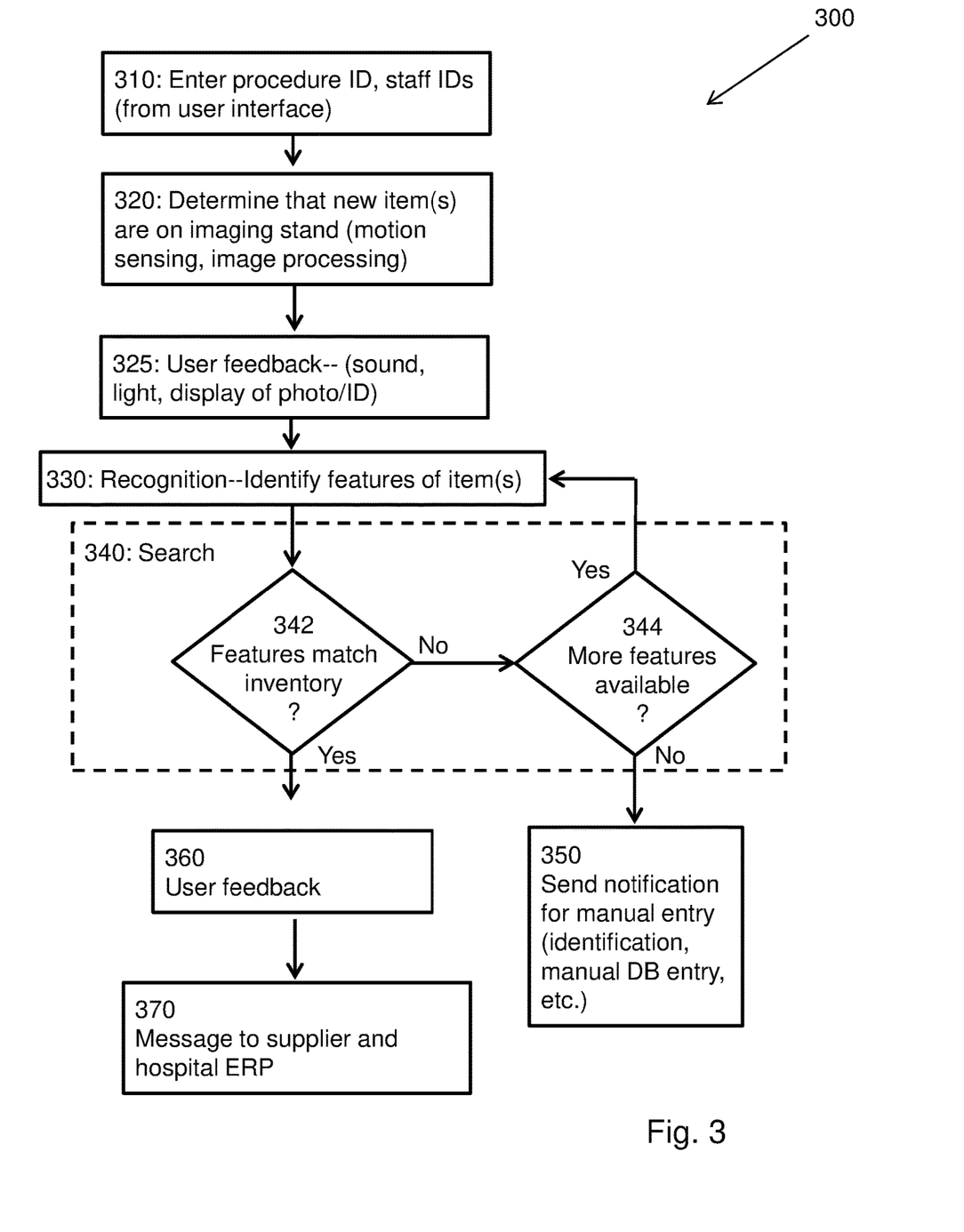
FIG. 3 is a flow diagram of a method for managing OR inventory, according to some embodiments of the present invention.

FIG. 3 is a flow diagram of a process 300 for managing operating room inventory, according to some embodiments of the present invention. At a first step 310, a surgical staff member typically initiates a process of recording (i.e., charging) surgical items by entering an identifier of the procedure to be performed. This may include a date and surgeon ID, for example. The information is entered at a user interface, such as a mobile device, which may be connected wirelessly to the imaging stand, as described above, or at a user interface integrated into the imaging stand.

Next, at a step 320, an item to be "consumed" during the surgery, such as an implant, is placed on the imaging stand. The item may be placed while still in packaging on which is printed identifying information. Identifying information (also referred to herein as, "recognition features") may include text, barcodes, and graphic images such as manufacturer logos. The packaging may also include an RFID. Identifying information may also be on the item itself, when it is delivered without packaging, such as etched text and symbols. As described further herein, the shape, size, and color of an item (whether in packaging or without packaging) may also provide recognition features for subsequent identification of an item.

The imaging stand employs one of several possible motion sensing technologies to identify placement of the item. For example, a passive infrared sensor (PIR sensor) may be positioned in the stand top to identify motion on the receptacle indicating placement of an item. The motion may then trigger the capture of a static image.

Alternatively, the digital camera may provide a streaming video feed to a processor that implements a motion sensing algorithm, identifying movement in the video stream images. Movement across the receptacle indicates that an object is being placed on the receptacle. When a change in successive frames of the video is identified, an item is being placed. Subsequently, when an image in a sequence of two subsequent frames does not change, the static image is determined to include the newly placed item.

Upon determining that a static image has been acquired a user notification may be provided, such as changing a color of an LED of the imaging stand, or playing an indicative sound, or by providing a notification on the display of the interactive device (step 325).

Next, at a step 330, the image is processed by the recognition service as described above. The recognition service, which may also be implemented in the user interface device rather than in the charge capture server, identifies positions of codes, text, and geometric figures in the image in order to provide such features to the search service (step 340). The search service at a step 342 performs searches of the various types of repositories in the one or more product databases 80. If there are no matches for one type of feature (step 344), a test is made for whether additional features may be extracted from the image by the recognition service. If so, then the process loops back to the recognition service at the step 330, continuing either until there is a match (at the step 342), or until no more features are available to be tested (at the step 344). The search service may also include algorithms or templates for combining multiple partial features to determine an item's identity. For example, if part of a barcode is not visible, but the part that is missing is a manufacturer's name, the manufacturer's name may be appear as text on the item (recognized by OCR), such that the two features may be merged to provide the information required for full identification.

If the identification is made, user feedback may be provided to the operating room staff (step 360). The mobile device, for example, may be configured to display the image of the item without an inventory identifier, to indicate that an image identifier was not determined. In some embodiments, this feedback may be provided so that operating room staff may repeat the placement of the item that was not identified, because the item's bar codes or other identifying features may not have been clear in the initial image. Typically, however, the repetition procedure is not employed, and instead the enrollment service is employed to identify the item (step 350).

When the search service succeeds in identifying the item, the search service typically transmits the item ID to the hospital ERP system, together with other recognition information, including the identifying information of the surgical procedure (step 370). In parallel, after step 325 is performed, the imaging stand is ready to accept a new item, and the capture of new images may be occurring in parallel with the processing of prior images.

Figure 4A:
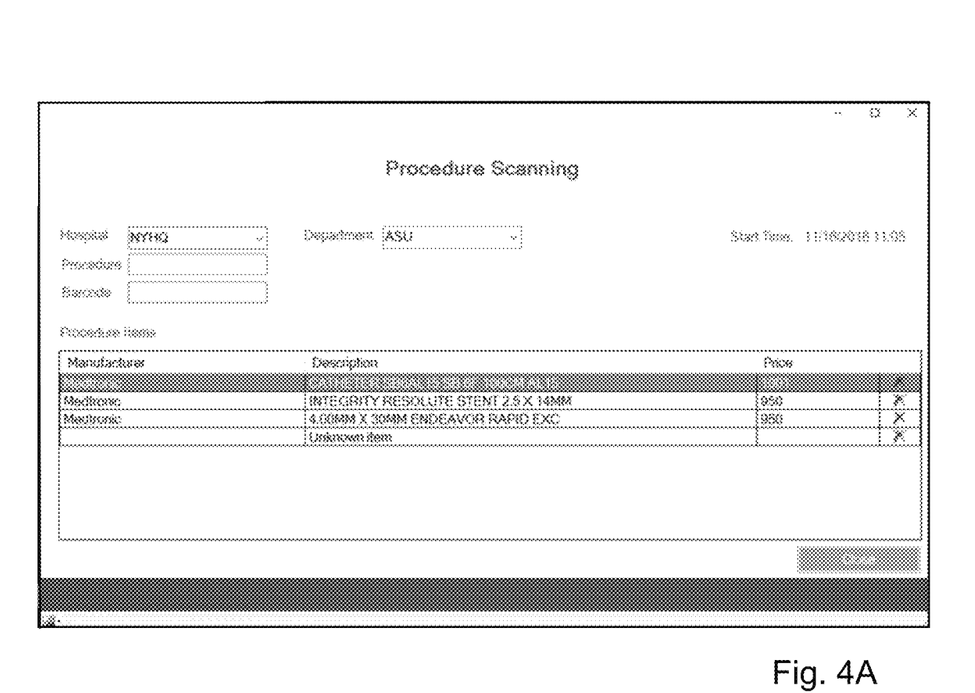
FIGS. 4A and 4B are screen shots of an application for managing OR inventory, according to some embodiments of the present invention.
Figure 4B:
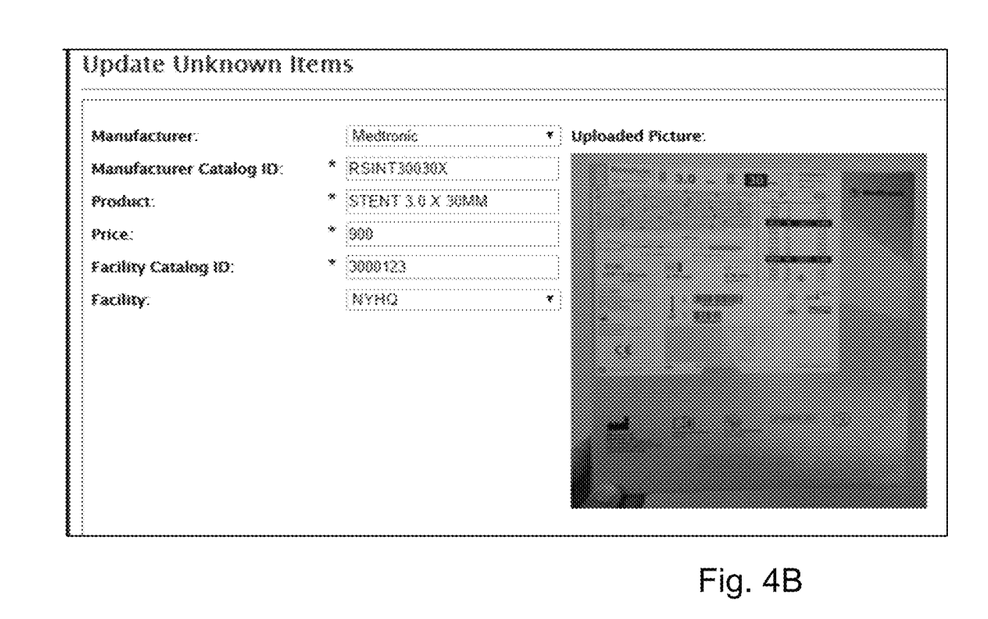

FIGS. 4A and 4B show two screenshots of an application providing a user interface to the enrollment service. FIG. 4A shows a screen that includes a listing of items recorded for entry into a surgical procedure. As indicated, the last item was not recognized by the recognition and search services. A user of the application may click on the unrecognized item and view the image of the item, in this case the sealed bag in which the item was delivered. The user may then complete the fields that were not sufficiently clear for automated completion. If the item is not in the database, the user may also add the item.

Computational aspects of system 20 and of process 300 may be implemented in digital electronic circuitry, or in computer hardware, firmware, software, or in combinations thereof. All or part of the system and process can be implemented as a computer program product, tangibly embodied in an information carrier, such as a machine-readable storage device or in a propagated signal, for execution by, or to control the operation of, data processing apparatus, such as a programmable processor, computer, or deployed to be executed on multiple computers at one website or distributed across multiple websites. Memory storage may also include multiple distributed memory units, including one or more types of storage media. Examples of storage media include, but are not limited to, magnetic media, optical media, and integrated circuits such as read-only memory devices (ROM) and random access memory (RAM). A computing system configured to implement the system may have one or more processors and one or more network interface modules. Processors may be configured as a multi-processing or distributed processing system. Network interface modules of one or more elements of the system may control the sending and receiving of data packets over networks.

It is to be understood that the scope of the present invention includes variations and modifications thereof which would occur to persons skilled in the art upon reading the foregoing description and which are not disclosed in the prior art.

The invention claimed is:

1. A system for managing surgical inventory in an operating room (OR) comprising:
   an imaging stand, to be positioned in or at the entrance to an operating room (OR), comprising a base receptacle on which to place surgical items, a post rising above the base receptacle, and a camera mounted at the top of the post, such that surgical items on the base receptacle are in the depth of field of the camera; and
   multiple processors and memory storage, the memory storage including instructions that when executed by the multiple processors implement steps comprising:
   acquiring an image, by the camera, of a surgical item placed on the base receptacle of the imaging stand;
   providing a notification at the imaging stand that the image is acquired;
   transmitting the image from the camera to a charge capture server including a recognition service and a search service;
   identifying in the image, by the recognition service, one or more recognition features of the surgical item by scanning for recognition feature types including printed text, a printed graphical image, a barcode, or a shape, and, in parallel, acquiring a new image, at the camera, of a new surgical item;
   searching, by the search service, one or more product databases for a match of a first recognition feature of the one or more recognition features, wherein the first recognition feature is of a first type, and, for no match of the recognition feature of the first type, searching for a match of one or more additional types of recognition features to determine, from the recognition features, an inventory identifier of the surgical item;
   upon successfully determining the inventory identifier, transmitting a message including the inventory identifier to a hospital inventory system to record use of the surgical item; and
   upon failing to determine an inventory identifier, transmitting the image to an application for manual identification of the surgical item.

2. The system of claim 1, wherein acquiring the new image comprises detecting a sequence of changing images and subsequently a sequence of static images, wherein the new image is one of the sequence of static images.

3. The system of claim 1, wherein acquiring the image comprises receiving the image from a video stream transmitted from the camera, and responsively determining by an image processing algorithm the presence of the surgical item in the image.

4. The system of claim 1, wherein one of the multiple processors and memory storage is integrated into the imaging stand.

5. The system of claim 1, wherein one of the multiple processors and memory storage are integrated into an interactive user device, wherein the interactive user device is one of a mobile device and an OR workstation.

6. The system of claim 1, wherein the imaging stand further comprises a transmitter for transmitting data from the camera to an interactive user device in the OR.

7. The system of claim 1, further comprising acquiring a procedure identifier at a user interface in the OR, wherein the procedure identifier is manually entered by a user, scanned from a printed record, or received from a storage medium.

8. The system of claim 1, further comprising an interactive user device configured to display the image and the inventory identifier to confirm determination of the inventory identifier.

9. The system of claim 1, further comprising an interactive user device configured by a mobile application to display the image without an inventory identifier to indicate that an image identifier was not determined.

10. The system of claim 1, wherein the multiple processors are processors operating on both an interactive user device and a cloud-based server.

11. The system of claim 1, wherein determining, from the recognition features, an inventory identifier of the surgical item comprises merging identifying aspects of multiple recognition features when part of a recognition feature is not visible.

12. The system of claim 1, wherein providing the user notification of image capture comprises providing a visual indicator by means of a light.

13. The system of claim 1, wherein determining an inventory identifier comprises completing a partial inventory identifier according to a predefined completion template.

14. The system of claim 1, wherein the message to a hospital inventory system is a first message and further comprising sending a second message to a supplier procurement system to order the surgical item.

15. The system of claim 1, wherein the recognition features include an RFID code acquired by an RFID reader of the imaging stand.

16. A method for managing surgical inventory in an operating room (OR), implemented by multiple processors and memory storage, the memory storage including instructions that when executed by the multiple processors implement the steps of:

acquiring an image, by the camera, of a surgical item placed on a receptacle of an imaging stand in the OR;

providing a notification at the imaging stand that the image is acquired;

transmitting the image from the camera to a charge capture server including a recognition service and a search service;

identifying in the image, by the recognition service, one or more recognition features of the surgical item by scanning for recognition feature types including printed text, a printed graphical image, a barcode, or a shape, and, in parallel, acquiring a new image, at the camera, of a new surgical item;

searching, by the search service, one or more product databases for a match of a first recognition feature of the one or more recognition features, wherein the first recognition feature is of a first type, and, for no match of the recognition feature of the first type, searching for a match of one or more additional types of recognition features to determine, from the recognition features, an inventory identifier of the surgical item;

upon successfully determining the inventory identifier, transmitting a message including the inventory identifier to a hospital inventory system to record use of the surgical item; and upon failing to determine an inventory identifier, transmitting the image to an application for manual identification of the surgical item.

\* \* \* \* \*